(12) United States Patent
Tamagawa et al.

(10) Patent No.: US 9,746,398 B2
(45) Date of Patent: Aug. 29, 2017

(54) APPARATUS AND METHOD FOR AUTOMATED ANALYSIS

(71) Applicant: JEOL Ltd., Tokyo (JP)

(72) Inventors: Takashi Tamagawa, Tokyo (JP); Yasuhiro Fukumoto, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 14/665,149

(22) Filed: Mar. 23, 2015

(65) Prior Publication Data

US 2015/0309060 A1   Oct. 29, 2015

(30) Foreign Application Priority Data

Mar. 24, 2014  (JP) .................................. 2014-59558

(51) Int. Cl.
*G01N 1/38* (2006.01)
*G01N 35/10* (2006.01)
*G01N 35/00* (2006.01)

(52) U.S. Cl.
CPC ........... *G01N 1/38* (2013.01); *G01N 35/0092* (2013.01); *G01N 35/1009* (2013.01); *G01N 2035/1032* (2013.01)

(58) Field of Classification Search
CPC .. G01N 1/38; G01N 35/0092; G01N 35/1009; G01N 2035/1032
See application file for complete search history.

(56) References Cited

U.S. PATENT DOCUMENTS 5,876,668 A * 3/1999 Kawashima ......... G01N 35/025
422/63

FOREIGN PATENT DOCUMENTS

JP             201054232 A      3/2010

* cited by examiner

*Primary Examiner* — Paul Hyun
(74) *Attorney, Agent, or Firm* — The Webb Law Firm

(57) ABSTRACT

An automated analyzer is offered which can dilute an analyte repeatedly without contamination due to carry-over and thus can yield reliable analysis results. The analyzer has an analyte turntable for holding analyte containers in which analyte is stored, a dilution turntable for holding dilution containers for storing a diluent, a dilution probe for aliquotting a liquid between two containers held on these two turntables, respectively, a diluent vessel for storing a diluent, and a diluent supply mechanism for supplying the diluent into the diluent vessel. The dilution probe has a function of aliquotting the diluent stored in the diluent vessel into the dilution containers held on the dilution turntable. The diluent vessel has a diluent discharging mechanism for discharging the diluent from inside the diluent vessel.

10 Claims, 13 Drawing Sheets

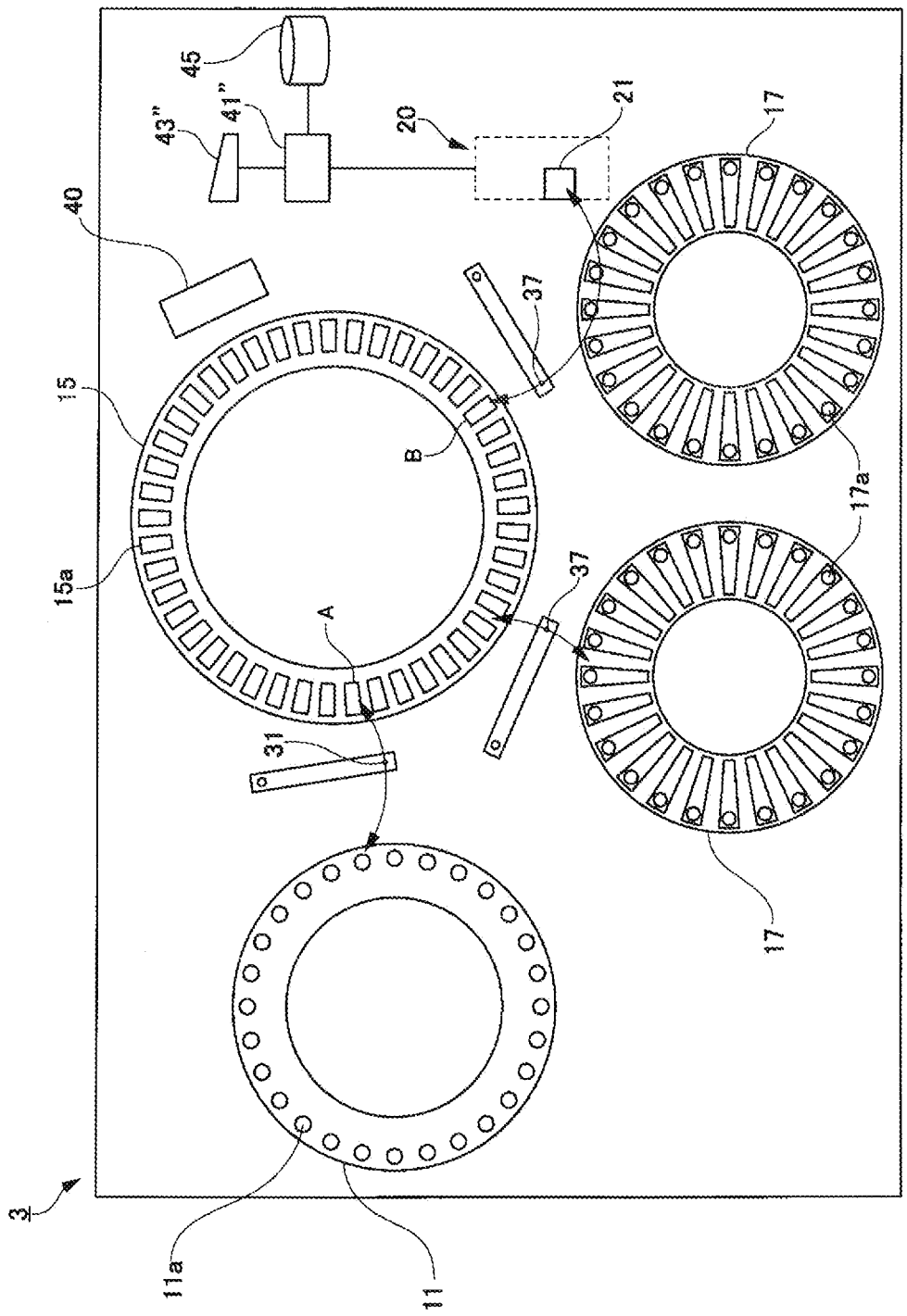

APPARATUS AND METHOD FOR AUTOMATED ANALYSIS

BACKGROUND OF THE INVENTION

Field of the Invention

The present invention relates to an apparatus and method for automated analysis and, more particularly, to an apparatus and method for automated chemical analysis wherein analytes are diluted.

Description of Related Art

A biochemical analyzer for analyzing biogenic substances contained in an analyte, such as blood or urine, is known as one type of automated analyzer. In this biochemical analyzer, in order to make concentrations of analytes lie within a measurement range, each analyte is diluted using physiological salt solution or deionized water.

A structure for diluting each analyte within a dilution pod mounted, for example, near an analyte aliquotting mechanism has been proposed as one automated analyzer wherein such dilution operations are performed. In this case, an analyte is aspirated by a probe from an analyte container conveyed into a given position on an analyte transport mechanism, and is dispensed into the dilution pod. A diluent is fed from a dilution bottle, and the analyte is diluted inside the pod. The dilution bottle has a tube which extends to the outside and which is in fluid communication with the dilution pod. The diluent is fed into the dilution pod by means of a pump or syringe through the tube. The analyte mechanism sucks an aliquot portion of each analyte diluted in the dilution pod and dispenses the analytes into reaction vessels, thus aliquotting the analyte (see JP-A-2010-54232).

In the automated analyzer involving the aforementioned dilution operations, however, an operation for aliquotting an analyte, which has been diluted in the single dilution pod, into reaction containers is performed consecutively for plural analytes. Therefore, the dilution pod is cleaned whenever an aliquotting operation is performed. However, if cleaning is not done sufficiently, the previously analyzed analyte remains in the dilution pod as it is. The remaining analyte mixes with an analyte next supplied into the dilution pod. This raises the concern that contamination is caused by so-called carry-over.

SUMMARY OF THE INVENTION

Accordingly, it is an object of the present invention to provide an apparatus and method which is adapted for automated analysis and which can dilute analytes without contamination due to carry-over, thus giving reliable analysis results.

An automated analyzer that achieves the above-described object in accordance with the teachings of the invention has container holders for holding containers in which a liquid is stored, a probe for aliquotting the liquid into two ones of the containers held by the container holders, a diluent vessel for storing a diluent, and a diluent supply mechanism for supplying the diluent into the diluent vessel. Furthermore, the probe has a function of aliquotting the diluent stored in the diluent vessel into any ones of the containers held by the container holders. The dilution vessel has a diluent discharging mechanism for discharging the diluent from inside the diluent vessel.

In the automated analyzer of this construction, even if a slight amount of analyte is carried into the diluent vessel by the probe, the diluent can be discharged from inside the diluent vessel through the diluent discharging mechanism and new diluent can be supplied into the diluent vessel from the diluent supply mechanism. Consequently, the diluent inside the diluent vessel is constantly replenished. If a diluting operation is repeated, contamination due to carry-over of analyte does not take place.

A method of automated analysis according to the present invention begins with aspirating a liquid from a first container by a probe. The liquid aspirated in the probe is dispensed into a second container. A diluent is supplied into a diluent vessel. The diluent in the diluent vessel is aspirated by the probe. The diluent aspirated in the probe is dispensed into the second container. These steps are performed repeatedly in a given procedure. After the diluent in the diluent vessel is aspirated by the probe, the diluent in the diluent vessel is discharged.

As described so far, according to the present invention, the diluent inside the diluent vessel can be constantly replenished and, therefore, dilution of analyte can be repetitively carried out without contamination due to carry-over. Hence, reliable analysis can be performed.

BRIEF DESCRIPTION OF THE DRAWINGS

FIG. 8 is a schematic representation of an automated analyzer according to a third embodiment of the present invention.

DESCRIPTION OF THE INVENTION

The preferred embodiments of the apparatus and method for automated analysis according to the present invention are hereinafter described in detail with reference to the accompanying drawings.

First Embodiment

Figure 1:
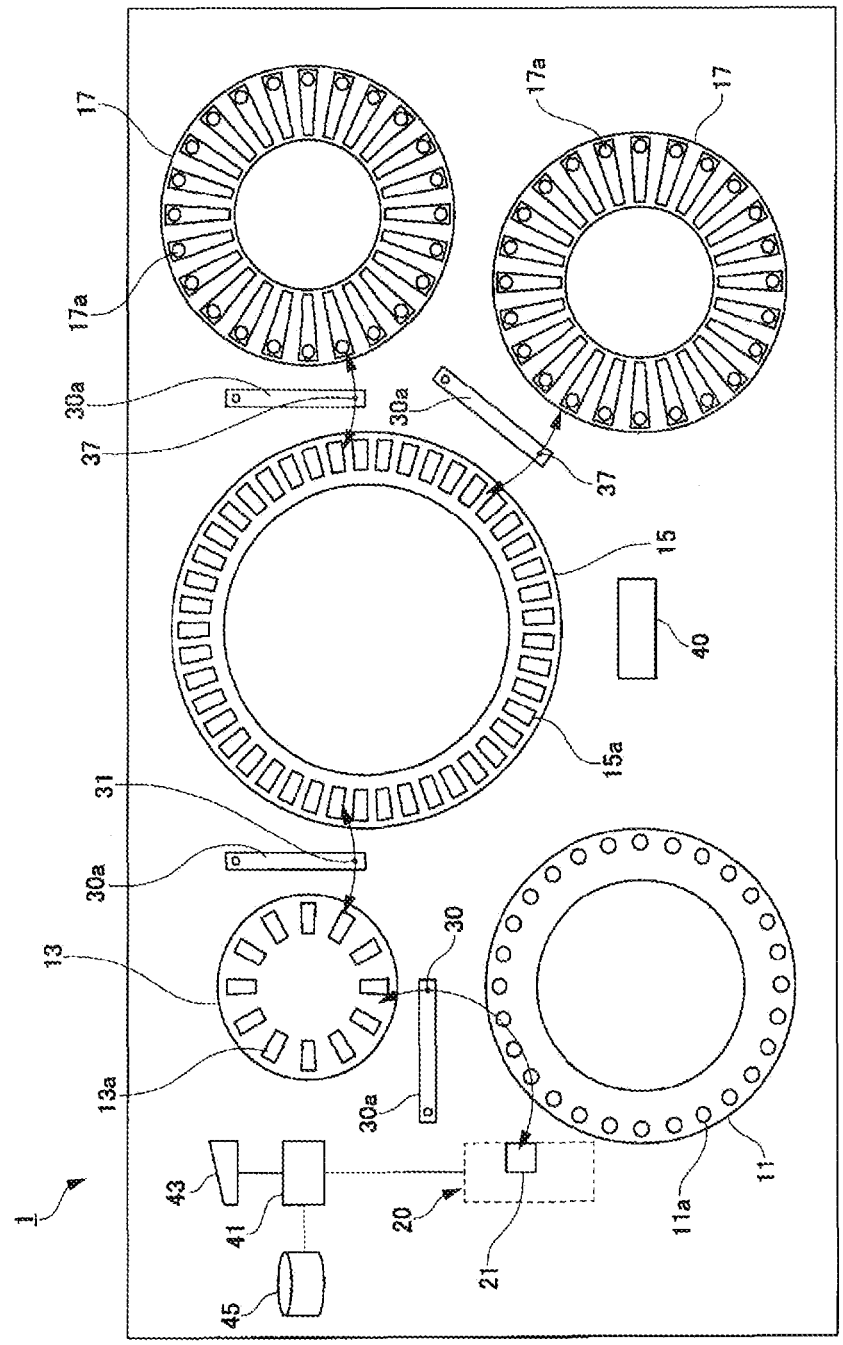
FIG. 1 is a schematic representation of an automated analyzer according to a first embodiment of the present invention.

Configuration of Automated Analyzer; Example of Aliquotting Diluent by Dilution Probe FIG. 1 is a schematic representation of an automated analyzer 1 according to a first embodiment of the present invention. As an example, the automated analyzer 1 is a biochemical analyzer for analyzing biogenic substances contained in analytes such as blood or urine.

The illustrated automated analyzer 1 includes a plurality of container holders 11, 13, 15, 17 and a diluent supply portion 20. Furthermore, the automated analyzer 1 has plural probes 30, 31, and 37 and a measurement section 40. The probe 30 is disposed between the container holders 11 and 13. The probe 31 is disposed between the container holders 13 and 15. Each of the probes 37 is disposed between the container holder 15 and a respective one of the container holders 17. In addition, the automated analyzer 1 includes a controller 41 for controlling the operation of these components, a manual control portion 43 for selecting and controlling these components through the controller 41, and a storage device 45. The components of the automated analyzer 1 are described in detail below.

[Container Holders 11, 13, 15, and 17]

It is assumed that each of the container holders 11, 13, 15, and 17 holds a plurality of containers and has a function of transporting the held containers in a given direction. As one example, the container holders 11, 13, 15, and 17 are devices which resemble turntables and rotate independently. Each of the turntable-like container holders 11, 13, 15, and 17 are configured to hold one or plural rows of containers 11a, 13a, 15a, or 17a along its outer periphery and to convey the held containers 11a, 13a, 15a, or 17a circumferentially bidirectionally.

Conveyance of the containers 11a, 13a, 15a, and 17a by the container holders 11, 13, 15, and 17, the directions of rotation of the turntable-like container holders 11, 13, 15, and 17, their angular positions, and their rotational speeds are controlled by the controller 41.

Among these components, the container holders 11, 13, 15, and 17 constructed in this way are arranged in this order from one end of the analyzer and constitute an analyte turntable 11, a dilution turntable 13, a reaction turntable 15, and reagent turntables 17. In the illustrated example, there are two reagent turntables 17. Alternatively, there may be only one reagent turntable 17 or there may be more than two reagent turntables 17 as the need arises.

The analyte turntable 11 is disposed close to the dilution turntable 13. The plurality of analyte containers 11a is held on the analyte turntable 11. Each of the analyte containers 11a stores a liquid analyte (sample), such as blood or urine, taken from an examinee.

The dilution turntable 13 is disposed near both analyte turntable 11 and reaction turntable 15. The plurality of dilution containers 13a is held on the dilution turntable 13. An analyte and a diluent are aliquotted into the dilution containers 13a. An analyte which may or may not be diluted with the diluent is stored in each dilution container 13a.

The reaction turntable 15 is disposed close to the dilution turntable 13 and also to the reagent turntables 17. The plurality of reaction containers 15a is held on the reaction turntable 15. An analyte or a diluted analyte is aliquotted and stored into the reaction containers 15a. Also, a reagent is aliquotted and stored in these reaction containers 15a. Chemical reactions are induced in the reaction containers 15a. For example, spectrophotometric cells are used as these reaction containers 15a.

The reagent turntables 17 are disposed close to the reaction turntable 15. The plurality of reagent containers 17a is held on each reagent turntable 17. A liquid reagent corresponding to one item of analysis of the analyte is stored in each reagent container 17a.

[Diluent Supply Portion 20]

Figure 2:
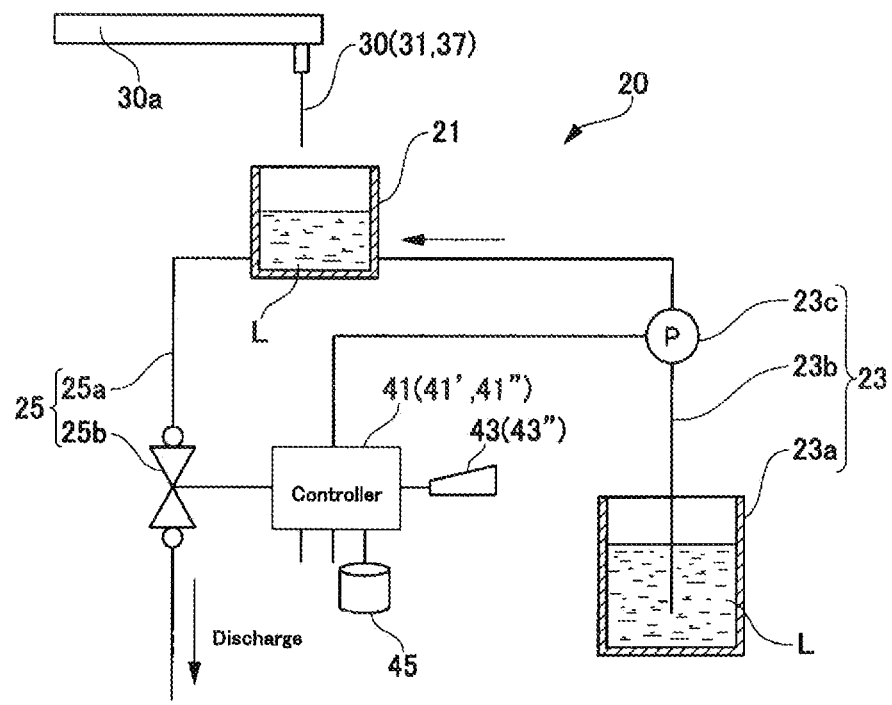
FIG. 2 is a schematic representation of a first configuration of a diluent supply portion of the automated analyzer shown in FIG. 1.

FIG. 2 is a schematic representation showing a first configuration of the diluent supply portion. As shown in FIGS. 1 and 2, the diluent supply portion 20 has a diluent vessel 21 and a diluent supply mechanism 23 for supplying diluent L into the diluent vessel 21. The diluent vessel 21 has a top opening through which the diluent probe 30 is inserted and the diluent L is drawn in. Physiological salt solution, deionized water, or other special solution is selected and used as the diluent L depending on the item of analysis.

As shown in FIG. 1, the diluent vessel 21 is disposed close to at least one of the analyte turntable 11 and the dilution turntable 13. It is assumed that the capacity of the diluent vessel 21 is nearly equal to or more than that of each dilution container 13a held on the dilution turntable 13. As shown in FIG. 2, the diluent vessel 21 has a diluent discharging mechanism 25 for discharging the diluent L from inside the diluent vessel 21. The discharging mechanism 25 is composed, for example, of a tube 25a connected to the bottom of the diluent vessel 21 and a discharge valve 25b mounted in this tube 25a. For instance, the discharge valve 25b is a solenoid valve that is controlled to be opened and closed by the controller 41 (described in detail later) such that the diluent L is discharged from the diluent vessel 21 at given timing.

The diluent supply mechanism 23 is designed to supply the diluent L into the diluent vessel 21, and composed of a tank 23a having a capacity sufficiently larger than that of the diluent vessel 21, a tube 23b for placing the tank 23a and the diluent vessel 21 in fluid communication with each other, and a suction pump 23c mounted in the tube 23b. The suction pump 23c feeds the diluent L from the tank 23a into the diluent vessel 21. The operation of the suction pump 23c is controlled by the controller 41 (described in detail later) such that the diluent L is supplied into the diluent vessel 21 at given timing and that the amount of the supplied diluent is adjusted to a given amount.

Figure 3:
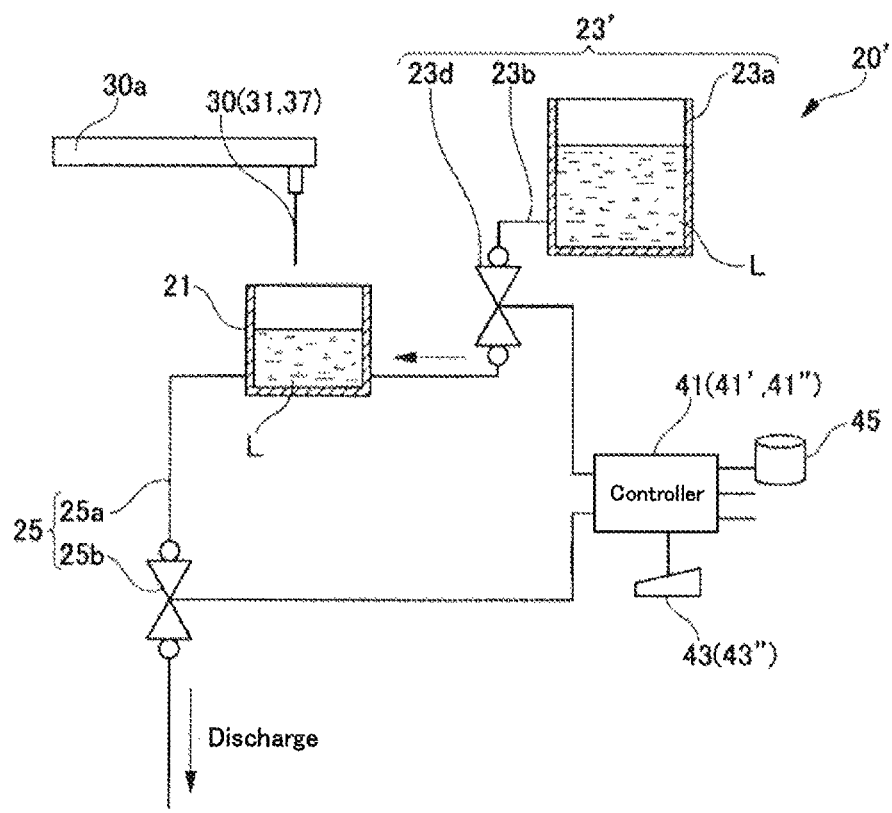
FIG. 3 is a schematic representation similar to FIG. 2, but showing a second configuration of the diluent supply portion of the automated analyzer shown in FIG. 1.

FIG. 3 is a schematic representation illustrating a second configuration of the diluent supply portion, 20'. This diluent supply portion 20' is similar to the diluent supply portion 20 shown in FIG. 2 except that a diluent supply mechanism 23' has a tank 23a located above the diluent vessel 21 and that a supply valve 23d is mounted in the tube 23b interconnecting the diluent vessel 21 and the tank 23a. For example, the supply valve 23d is a solenoid valve. The diluent L is supplied from the higher tank 23a into the lower diluent vessel 21 by siphonage by opening the supply valve 23d. The supply valve 23d is opened and closed under control of the controller 41 (described in detail later) such that the diluent L is supplied into the diluent vessel 21 at giving timing and that the amount of supply is adjusted to a given amount.

The diluent supply portion 20 is not restricted to the configurations described in connection with FIGS. 2 and 3 as long as the supply portion 20 has the diluent supply mechanism 23 capable of supplying the diluent L into the diluent vessel 21 and the diluent discharging mechanism 25 capable of discharging the diluent L from the diluent vessel 21.

[Probes 30, 31, and 37]

The probes 30, 31, and 37 shown in FIG. 1 operate to deliver an aliquot portion of a liquid between two containers held by two ones of the container holders 11, 13, 15, and 17. The probes 30, 31, and 37 can draw in and deliver the liquid. These probes 30, 31, and 37 are so held that they depend from the front ends of arms 30a. Each of the arms 30a is composed of a pillar portion standing upright from a position close to one of the container holders 11, 13, 15, and 17 and a support portion extending horizontally from near the upper end of the pillar portion. The probes 30, 31, and 37 are held to the front ends of the support portions of the respective arms. Consequently, as indicated by the arrows in FIG. 1, the probes 30, 31, and 37 can move along orbits drawn by the front ends of the arms 30a. Furthermore, these probes can move up and down over these orbits.

The operation of the arms 30a to move the probes 30, 31, and 37, the operation of the probes 30, 31, and 37 to draw in and deliver liquid, and the operation of the container holders 11, 13, 15, and 17 are controlled by the controller 41 (described in detail later). Water is held in the probes 30, 31, and 37 to cause the liquid drawn in the probes 30, 31, and 37 to be discharged from the probes 30, 31, and 37. This discharging water is herein referred to as the pushing water and may be used as a diluent as described later in connection with a method of automated analysis. Deionized water or physiological salt solution is used as the pushing water. These probes 30, 31, and 37 are dilution probe 30, analyte probe 31, and reagent probes 37, respectively, and are constructed as described below.

The dilution probe 30 is disposed between the analyte turntable 11 and the dilution turntable 13. The dilution probe 30 is inserted in one of the analyte containers 11a held on the analyte turntable 11 and operates to draw in a given amount of liquid (analyte in this example). The dilution probe 30 dispenses the aspirated analyte into the dilution containers 13a held on the dilution turntable 13. The dilution probe 30 is inserted in the diluent vessel 21 and aspirates a given amount of diluent. The dilution probe 30 dispenses the aspirated diluent into the dilution containers 13a held on the dilution turntable 13.

That is, the dilution probe 30 acts to aliquot the diluent. Therefore, the orbit of the dilution probe 30 lies over the holding container (11a) holding portions on the analyte turntable 11, over the dilution container (13a) holding portions on the dilution turntable 13, and over the diluent vessel 21. That is, the diluent vessel 21 is located over the orbit of the dilution probe 30.

The analyte probe 31 is positioned between the dilution turntable 13 and the reaction turntable 15. The analyte probe 31 is inserted into a selected one of the dilution containers 13a held on the dilution turntable 13 and draws in a given amount of analyte or diluted analyte. The dilution probe 31 dispenses the analyte, which may or may not be diluted, into the reaction containers 15a held on the reaction turntable 15.

This analyte probe 31 can aliquot a liquid into plural ones of the reaction containers 15a held on the reaction turntable 15 according to the need.

Each of the reagent probes 37 is disposed between the reaction turntable 15 and a respective one of the reagent turntables 17. Each reagent probe 37 is inserted into a selected one of a respective one of the reagent containers 17a held on the reagent turntable 17 and draws in a given amount of reagent. The reagent probe 37 dispenses the aspirated reagent into the reaction containers 15a held on the reaction turntable 15.

[Measurement Section]

The measurement section 40 is an absorptiometer, for example, and operates to measure the absorbance of each analyte that has reacted with the reagent dispensed into each reaction container 15a. This measurement section 40 is disposed opposite to the wall surface of each reaction container 15a held on the reaction turntable 15. Timing at which the measurement section 40 makes a measurement is controlled by the controller 41 described next.

[Controller 41]

The controller 41 controls the operations of the various components described so far. In particular, the controller 41 controls the operations of the container holders 11, 13, 15, 17, the diluent supply portion 20, probes 30, 31, 37, and measurement section 40 such that analytes are analyzed in the procedure described in the following method of automated analysis.

[Manual Control Portion 43]

Figure 4:
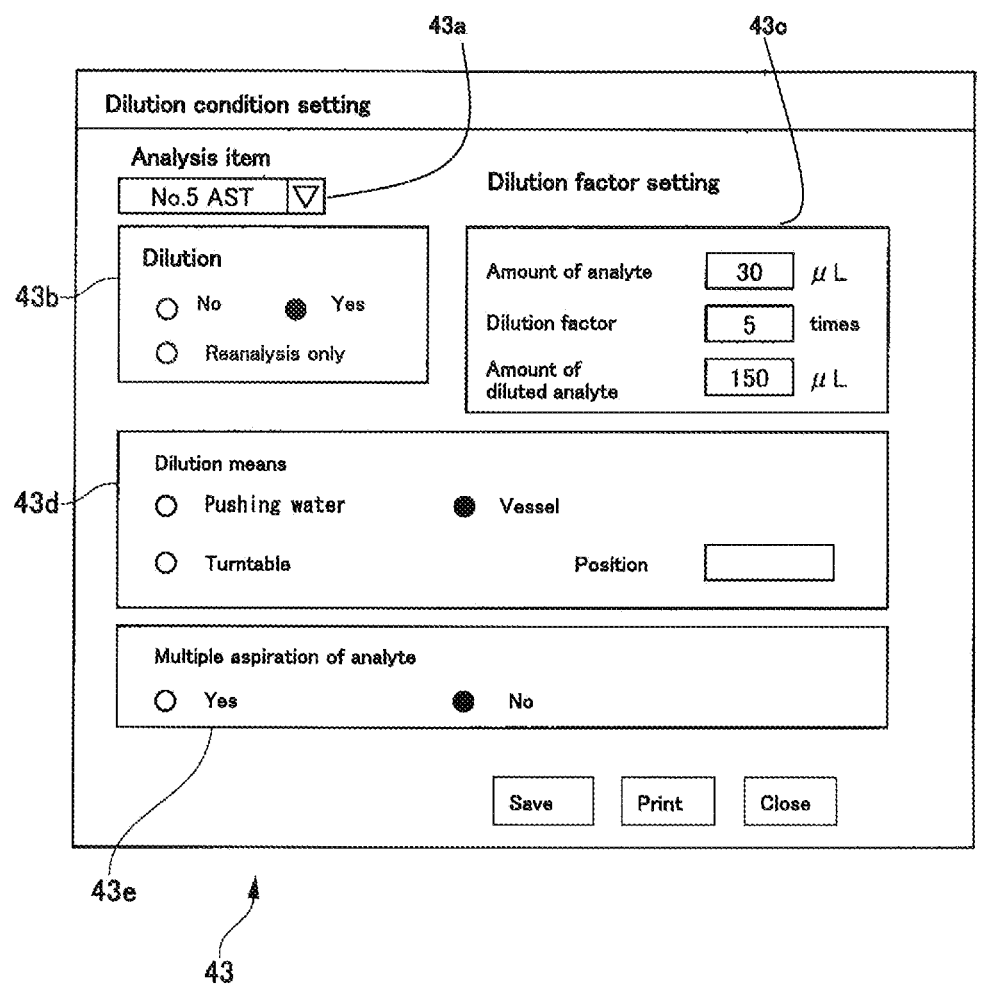
FIG. 4 is a schematic representation of a manual control portion of the automated analyzer shown in FIG. 1.

The manual control portion 43 permits one to select a control program to be run by the controller 41. This manual control portion 43 has a display device on which a condition setting screen, for example, corresponding to items of analysis is displayed. A control program is selected by manipulating a touch panel or cursor. FIG. 4 schematically shows the configuration of the manual control portion. As one example, a dilution condition setting screen portion of the condition setting screen corresponding to the items of analysis is shown. A plurality of setting portions 43a-43e is displayed on the setting screen.

Of these setting portions, the analysis item setting portion 43a permits one to select a desired item of analysis from a plurality of items of analysis previously stored in the storage device. An item of analysis "No. 5", i.e., concentration analysis of AST (aspartate aminotransferase), is selected here as one example.

The dilution setting portion 43b permits one to select whether each analyte is "not diluted" or "diluted". In this example, each analyte is "diluted".

The dilution factor setting portion 43c permits one to set "amount of analyte", "dilution factor", and "amount of diluted analyte". In this example, the "amount of analyte", "dilution factor", and "amount of diluted analyte" are set to 30 μl (microliters), 5 times, and 150 μl respectively.

The dilution means setting portion 43d permits one to select a dilution means for diluting each analyte. The dilution means is selected, for example, from "dilution with pushing water", "diluent vessel", and "turntable dilution". When the "dilution with pushing water" is selected, dilution is done using the pushing water inside a probe as a diluent. When the "diluent vessel" is selected, dilution is done using the diluent inside the diluent vessel. When the "turntable dilution" is selected, dilution is done using the diluent stored in the analyte containers on the analyte turntable. This "turntable dilution" is used when a special diluent is used. When this "turntable dilution" is selected, an input is made to select a position where an analyte container storing the special diluent is held on the analyte turntable.

When the "diluent vessel" using aspiration from the diluent vessel or the "turntable dilution" is selected through the diluting means setting portion 43d, the consecutive aspiration setting portion 43e permits one to select whether the analyte is continuously "aspirated" or "not aspirated" by the probe that has drawn in the diluent. In this example, non-continuous aspiration is selected.

The dilution condition setting screen has been shown so far as one example of setting of a control program using the manual control portion 43. Furthermore, an analyte type (whether serum or urine) setting screen and other condition setting screen may be displayed. Setting of a control program through the manual control portion 43 is not restricted to the above-described manner in which each item of analysis is set. Alternatively, dilution conditions or other conditions may be set for each analyte.

[Storage Device 45]

The storage device 45 shown in FIGS. 1-3 is connected with the controller 41. A control program, for example, indicating timings at which the various components are operated for each item of analysis is previously stored in the storage device 45.

[Other Components]

The above-described automated analyzer 1 has other components (not shown) in addition to the above-described components. The other components include stirrers and probe cleaners. The stirrers are placed in requisite locations of the container holders 13 and 15. The probe cleaners are located in the routes of the probes 30, 31, and 37 which do not affect aliquotting operations using the probes 30, 31, and 37. Whenever the probes 30, 31, and 37 perform aliquotting operations, the probe cleaners clean the probes.

Method of Automated Analysis

Figure 5A:
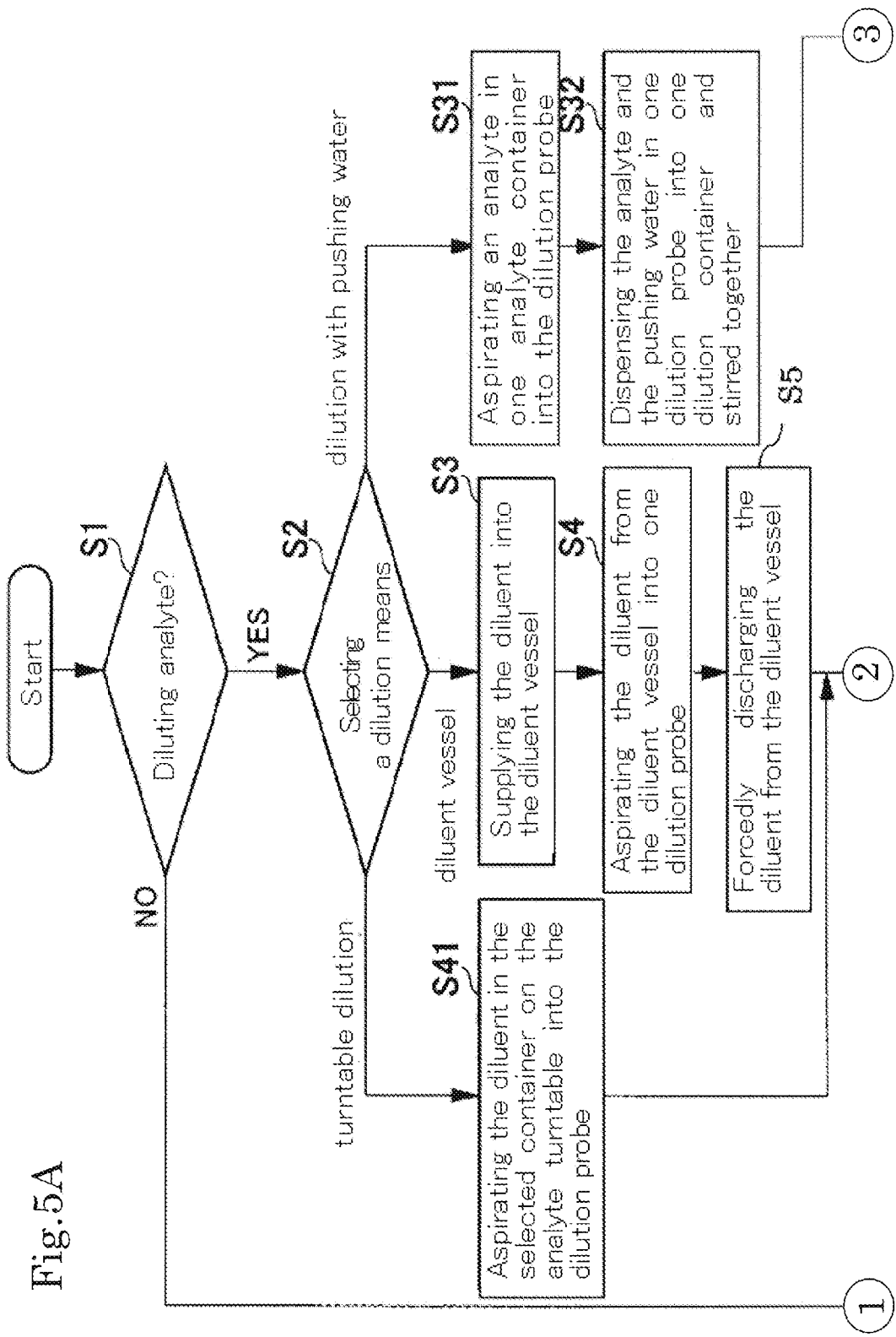
FIGS. 5A and 5B are flowcharts illustrating a method of automated analysis using the automated analyzer shown in FIG. 1.
Figure 5B:
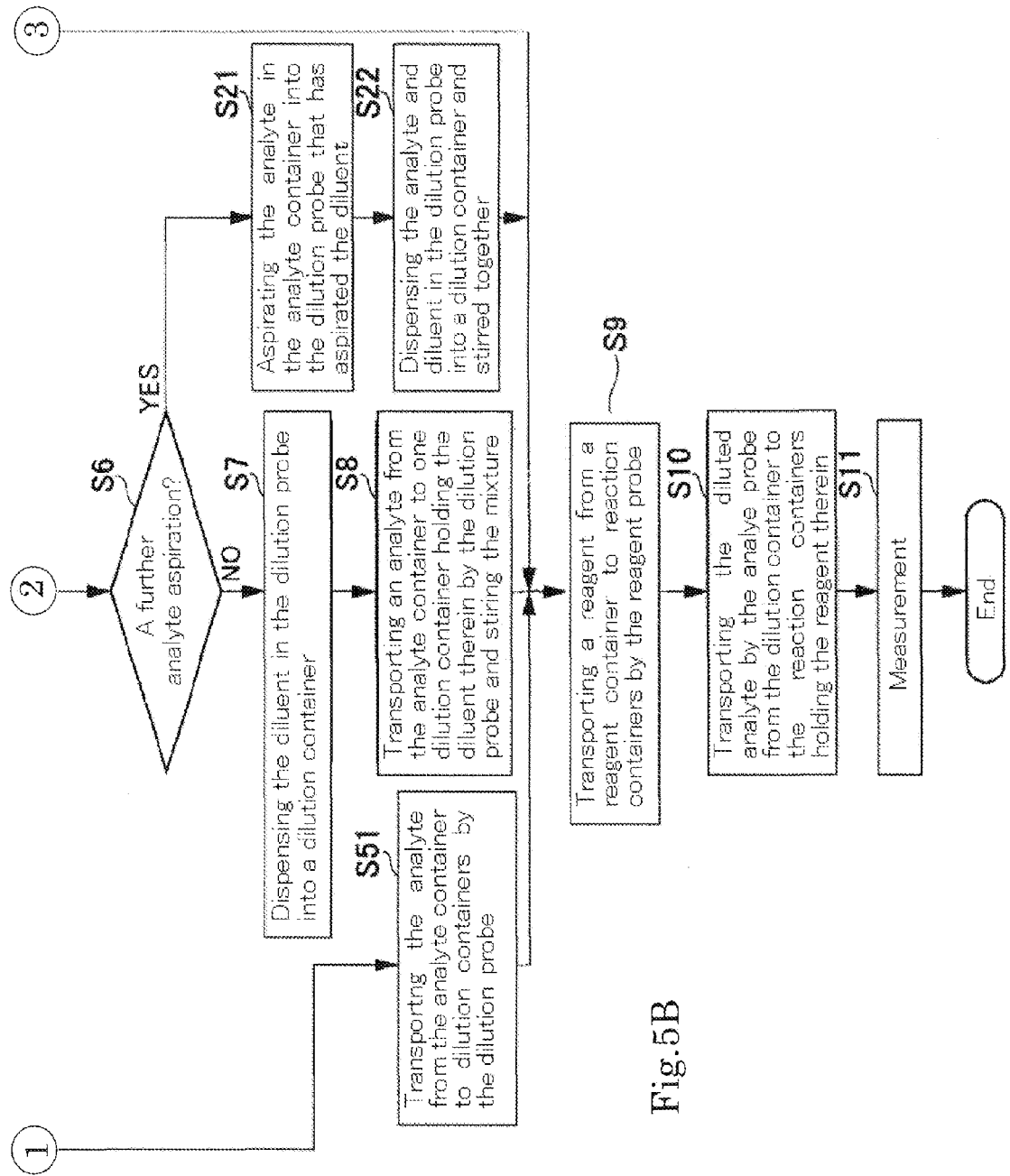

FIGS. 5A and 5B are flowcharts illustrating a method of automated analysis using the automated analyzer 1 according to the first embodiment. The procedure of the method of automated analysis executed by the controller 41 of the automated analyzer 1 is described below by referring to the flowcharts of FIGS. 5A and 5B and also to FIGS. 1-4. A description of the operation for cleaning the probes is omitted here. It is assumed that whenever the probes 30, 31, and 37 perform aliquotting operations, they are cleaned.

Prior to the procedure of automated analysis illustrated in the flowcharts of FIGS. 5A and 5B, items of analysis and a control program to be run by the controller 41 are selected and set through the manual control portion 43 shown in FIG. 4. The analyte turntable 11 shown in FIG. 1 holds the plurality of analyte containers 11a storing analytes. The dilution containers 13a are held on the dilution turntable 13. The reaction containers 15a are held on the reaction turntable 15. Each reagent turntable 17 holds the reagent containers 17a storing reagents corresponding to the set items of analysis. Then, the analysis is made to progress as follows.

First, in step S1, a decision is made as to whether each analyte is diluted or not. If "dilution" of the analyte is selected through the dilution setting portion 43b of the manual control portion 43 already shown in FIG. 4, it is determined that dilution is done (YES), and control proceeds to the next step S2.

If "non-dilution" of the analyte is selected through the dilution setting portion 43b of the manual control portion 43, it is determined that dilution is not done (NO), and control goes to step S51.

In step S2, a dilution means is selected. If the "diluent vessel" using aspiration from the diluent vessel is selected through the diluting means setting portion 43d of the manual control portion 43 already shown in FIG. 4, control goes to step S3.

If "dilution with pushing water" from probes is selected through the diluting means setting portion 43d of the manual control portion 43, control goes to step S31. If "turntable dilution" is selected, control goes to step S41.

In step S3, the diluent L is supplied into the diluent vessel. As already described in connection with FIG. 2, the suction pump 23c is driven to feed the diluent L from the tank 23a into the diluent vessel 21. Alternatively, as already described in connection with FIG. 3, the diluent L is supplied from the tank 23a into the diluent vessel 21 by opening the supply valve 23d. At this time, an amount of diluent corresponding to the setting on the dilution factor setting portion 43c of the manual control portion 43 shown in FIG. 4 is supplied into the diluent vessel 21.

In step S4, the diluent L is aspirated from the diluent vessel into one dilution probe. In this example, the dilution probe 30 shown in FIG. 1 is inserted into the diluent vessel 21, and the diluent inside the diluent vessel 21 is aspirated.

In step S5, the diluent is forcedly discharged from the diluent vessel. In this example, as already described in connection with FIG. 2 or 3, all the diluent in the diluent vessel 21 is discharged by opening the discharge valve 25b mounted in the diluent vessel 21. Thus, whenever an aspiration of the diluent L in step S4 is completed, the diluent L in the diluent vessel 21 is forcedly discharged.

In step S6, a decision is made as to whether a further analyte aspiration is immediately performed. A probe that has aspirated the diluent L (in this example, the dilution probe 30) has selected "No Subsequent Aspiration" of analyte through the consecutive aspiration setting portion 43e of the manual control portion 43 already shown in FIG. 4, it is determined that a subsequent aspiration of analyte is not done (NO), and control goes to step S7.

If a subsequent aspiration of analyte by the probe (in this example, the dilution probe 30) that has aspirated the diluent L is selected through the consecutive aspiration setting portion 43e of the manual control portion 43, it is determined that a subsequent aspiration of analyte is done (YES), and control goes to step S21.

In step S7, the diluent L in the dilution probe is dispensed into a dilution container. In this example, the dilution probe 30 shown in FIG. 1 is moved into a position above one dilution container 13a held on the dilution turntable 13, and the diluent L is dispensed into the dilution container 13a.

In step S8, the dilution probe transports aliquot of an analyte from the analyte container to one dilution container holding the diluent L therein and to stir the mixture. In particular, the dilution probe 30 shown in FIG. 1 first aspirates an analyte from inside a given analyte container 11a held on the analyte turntable 11 and dispenses the aspirated analyte into the dilution container 13a storing the diluent L on the dilution turntable 13. Then, the diluent L and the analyte stored in the dilution containers 13a are stirred together by the stirrers (not shown), thus producing a diluted analyte.

In step S9, a reagent is transported from a reagent container to reaction containers by the reagent probe. In this example, a reagent inside one reagent container 17a is aspirated by a corresponding one of the reagent probes 37 shown in FIG. 1, and the aspirated reagent is dispensed into the reaction containers 15a held on the reaction turntable 15.

In step S10, the diluted analyte is transported by the analyte probe from the dilution container to the reaction containers holding the reagent therein. In this example, the diluted analyte is first aspirated from inside one dilution container 13a storing the diluted analyte on the dilution turntable 13 by the analyte probe 31 shown in FIG. 1, and the aspirated diluted analyte is dispensed into the reaction containers 15a storing a reagent on the reaction turntable 15. Then, the diluted analyte and reagent stored in the reaction containers 15a are stirred together by the stirrers (not shown).

In step S11, a measurement is performed. In this example, the reaction container 15a in which the diluted container and the reagent are stored in step S10 is moved into a position opposite to the measurement section 40 shown in FIG. 1, and the absorbance of the analyte that has reacted with the reagent is measured. Thus, a measurement for the set item or items of measurement is ended.

If the decision at the step S6 is YES indicating that a subsequent aspiration is done, i.e., a subsequent aspiration of an analyte is selected through the consecutive aspiration setting portion 43e of the manual control portion 43 already shown in FIG. 4, control goes to step S21.

In this step S21, the analyte in the analyte container is aspirated into the dilution probe that has aspirated the diluent L. That is, in step S4, after the diluent L is aspirated into the dilution probe from the diluent vessel, an analyte is subsequently aspirated into the dilution probe that has aspirated the diluent L. In this example, immediately after the diluent inside the diluent vessel 21 is aspirated by the dilution probe 30 shown in FIG. 1, an analyte in a given analyte container 11a held on the analyte turntable 11 is aspirated.

In step S22, the analyte and diluent in the dilution probe are dispensed into a dilution container and stirred together. In this step, the analyte and diluent in the dilution probe 30 shown in FIG. 1 are dispensed into one dilution container 13a on the dilution turntable 13 and stirred together by the stirrer (not shown), thus producing a diluted analyte. Then, steps S9-S11 are performed. The measurement for the set items of analysis is ended.

If the decision at the step S2 is that "dilution with pushing water" is selected, control goes from step S2 to step S31, where an analyte in one analyte container is aspirated into the dilution probe. In this step, the dilution probe 30 shown in FIG. 1 is inserted into one analyte container 11a held on the analyte turntable 11, and the analyte in the analyte container 11a is aspirated. It is assumed that a diluent is held in the dilution probe 30 as the pushing water for dispensing the liquid inside the dilution probe 30.

In step S32, the analyte and the pushing water in one dilution probe are dispensed into one dilution container and stirred together. In this step, the pushing water in the dilution probe 30 shown in FIG. 1 is used as a diluent. This diluent is dispensed into the dilution containers 13a held on the dilution turntable 13 together with the analyte aspirated in the dilution probe 30 and stirred by the stirrers (not shown), thus producing diluted analytes. Then, steps S9-S11 are performed, and the measurement for the set items of analysis is ended.

If the decision at the step S2 is that "turntable dilution" is selected, control goes from step S2 to step S41, where the diluent in the selected container on the analyte turntable is aspirated into the dilution probe. In this step, the dilution probe 30 shown in FIG. 1 is inserted into the given analyte container 11a held on the analyte turntable 11, and the diluent L in the analyte container 11a is aspirated. Then, steps S6-S11 are performed and the measurement for the set items of analysis is ended.

If the decision at the step S1 is NO indicating that the analyte is not diluted, i.e., if "non-dilution" of the analyte is selected through the dilution setting portion 43b of the manual control portion 43 already shown in FIG. 4, it is determined that dilution is not done (NO), and control goes to step S51.

In this step S51, the dilution probe transports the analyte from the analyte container to dilution containers. In this step, the dilution probe 30 shown in FIG. 1 aspirates the analyte from inside the given analyte container 11a held on the analyte turntable 11. The probe dispenses the aspirated analyte into hollow ones of the dilution containers 13a held on the dilution turntable 13.

Subsequently, steps S9-S11 are performed. In the step S10, the analyte probe 31 shown in FIG. 1 aspirates an undiluted analyte from inside one dilution container 13a on the dilution turntable 13 and dispenses the aspirated analyte into the reaction containers 15a where a reagent is stored on the reaction turntable 15. Then, the analyte and the reagent are stirred together. Thus, the measurement for the set items of analysis is ended.

The processing sequence of steps S1-S51 described so far is carried out repeatedly and successively for a plurality of analytes. Therefore, a decision step (not shown) may be provided after the step S11 to make a decision as to whether a measurement for a set number (n) of analytes is ended, and the steps S1-S51 may be repeated until it is determined that the number n is reached.

Advantageous Effects of First Embodiment

The automated analyzer 1 according to the first embodiment described so far is so configured that the dilution probe 30 for aliquoting an analyte from a selected one of the analyte containers 11a into the dilution containers 13a aliquots the diluent from the diluent vessel 21 into the dilution containers 13a. Especially, the diluent vessel 21 has the diluent discharging mechanism 25. Therefore, if a slight amount of analyte is carried into the diluent vessel 21 by this dilution probe 30, carry-over of the analyte in the diluent vessel 21 can be prevented by discharging the diluent inside the diluent vessel 21 from the diluent discharging mechanism 25 and supplying a new diluent into the diluent vessel 21 from the diluent supply mechanism 23.

Especially, the analyte carry-over inside the diluent vessel 21 can be prevented more effectively by forcing the diluent out of the diluent vessel 21 whenever an aspiration of the diluent by the dilution probe 30 ends under control of the controller 41 as described in connection with the method of automated analysis using the automated analyzer 1. As a result, use of the automated analyzer 1 permits repetitive dilution of analyte without suffering from contamination due to carry-over. Hence, reliable analysis can be performed.

Furthermore, the automated analyzer 1 and method of automated analysis according to the first embodiment are so configured that a diluent is supplied into the diluent vessel 21 from the diluent supply mechanism 23 and so it is not necessary to prepare and arrange any special container storing a diluent. This can dispense with labor of the operator. On the other hand, where a container holding a diluent is held on the analyte turntable 11 and the diluent is aliquoted from this container using the dilution probe 30, labor is required to hold the container storing the diluent onto the analyte turntable 11. Furthermore, in this case, the number of analyte containers 11a storing analytes and held on the analyte turntable 11 must be reduced by the number of containers storing a diluent and held on the analyte turntable 11. This leads to a decrease in the number of analytes that can be automatically analyzed. In the automated analyzer 1 of the present first embodiment, the number of analytes to be analyzed can be maintained.

In addition, the automated analyzer 1 of the first embodiment is specially equipped with the diluent vessel 21 storing only a diluent and, therefore, when continuous analysis, for example, using a plurality of types of diluent is performed, it is only necessary that a diluent consisting of a physiological salt solution or other special solution (such as hemolysate needed for measurement of HbAlc) be stored in the diluent vessel 21 and that deionized water be used as the pushing water for the dilution probe 30 that might be used as a diluent. Therefore, if the pushing water is used as a diluent, it is not necessary to use physiological salt solution as this pushing water. Consequently, continuous analysis can be performed at low cost.

In the first embodiment described so far, a diluent is aspirated from the diluent vessel into the dilution probe in the step S4 as illustrated in FIGS. 5A and 5B. Whenever this aspirating step ends, the diluent is forced out of the diluent vessel in the step S5. Note that the manner in which the diluent is discharged from the diluent vessel is not restricted to this method. For example, where a plurality of diluted analytes is successively created from the same analyte and analyzed, a decision step may be added to determine whether this analysis is completed. Whenever an operation for preparing plural diluted analytes from one analyte is completed, the diluent may be forced out of the diluent vessel.

Second Embodiment

Figure 6:
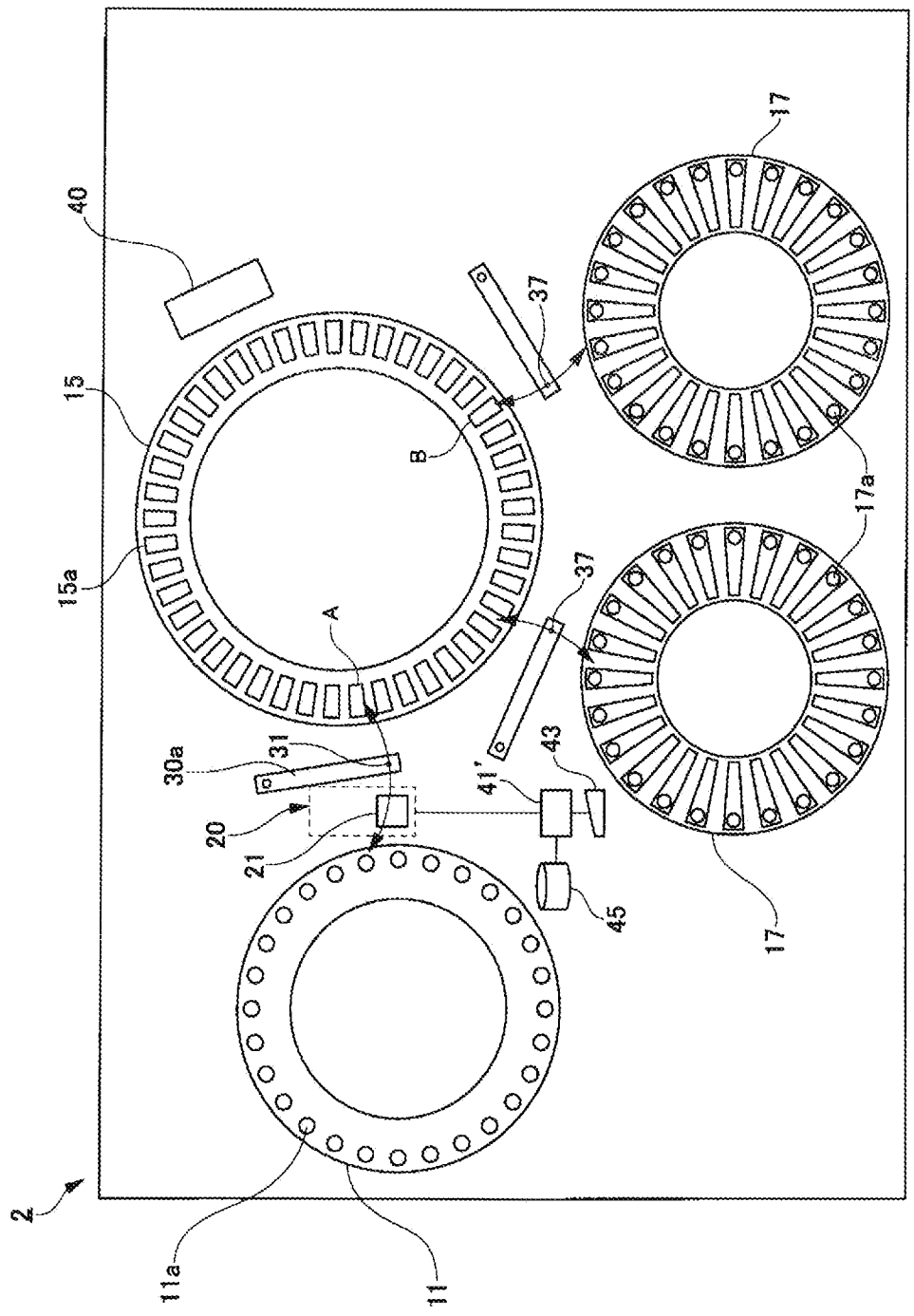
FIG. 6 is a schematic representation of an automated analyzer according to a second embodiment of the present invention.

Configuration of Automated Analyzer; Example of Aliquotting of Diluent by Analyte Probe FIG. 6 schematically shows the configuration of an automated analyzer according to a second embodiment of the present invention. This automated analyzer, 2, is similar to the automated analyzer 1 of the first embodiment except that the dilution turntable 13 and dilution probe 30 (FIG. 1) mounted in the automated analyzer 1 are dispensed with. Furthermore, a controller 41' operates the analyte probe 31 to aliquot the diluent from the diluent vessel 21. Those components of the automated analyzer 2 which are identical to their respective counterparts of the automated analyzer 1 of the first embodiment are indicated by the same reference numerals as in FIG. 1 and a description thereof is omitted. Only the differences are described.

In this automated analyzer 2, the analyte turntable 11, reaction turntable 15, and reagent turntables 17 are arranged in turn from one end of the analyzer. The analyte probe 31 is disposed between the analyte turntable 11 and the reaction turntable 15. Each reagent probe 37 is disposed between the reaction turntable 15 and a respective one of the reagent turntables 17.

The diluent supply portion 20 is similar in configuration to that of the first embodiment and configured as already described in connection with FIGS. 2 and 3. The diluent supply portion 20 includes the diluent vessel 21 that is placed close to at least one of the analyte turntable 11 and the reaction turntable 15. The analyte probe 31 is mounted in a position where it can be moved by its arm 30a.

The controller 41' controls the operation of the analyte probe 31 such that a diluent is aliquotted from the diluent vessel 21 as described next in connection a method of automated analysis. The measurement section 40, the manual control portion 43, the storage device 45, and other components are similar to their respective counterparts of the first embodiment.

Method of Automated Analysis

Figure 7A:
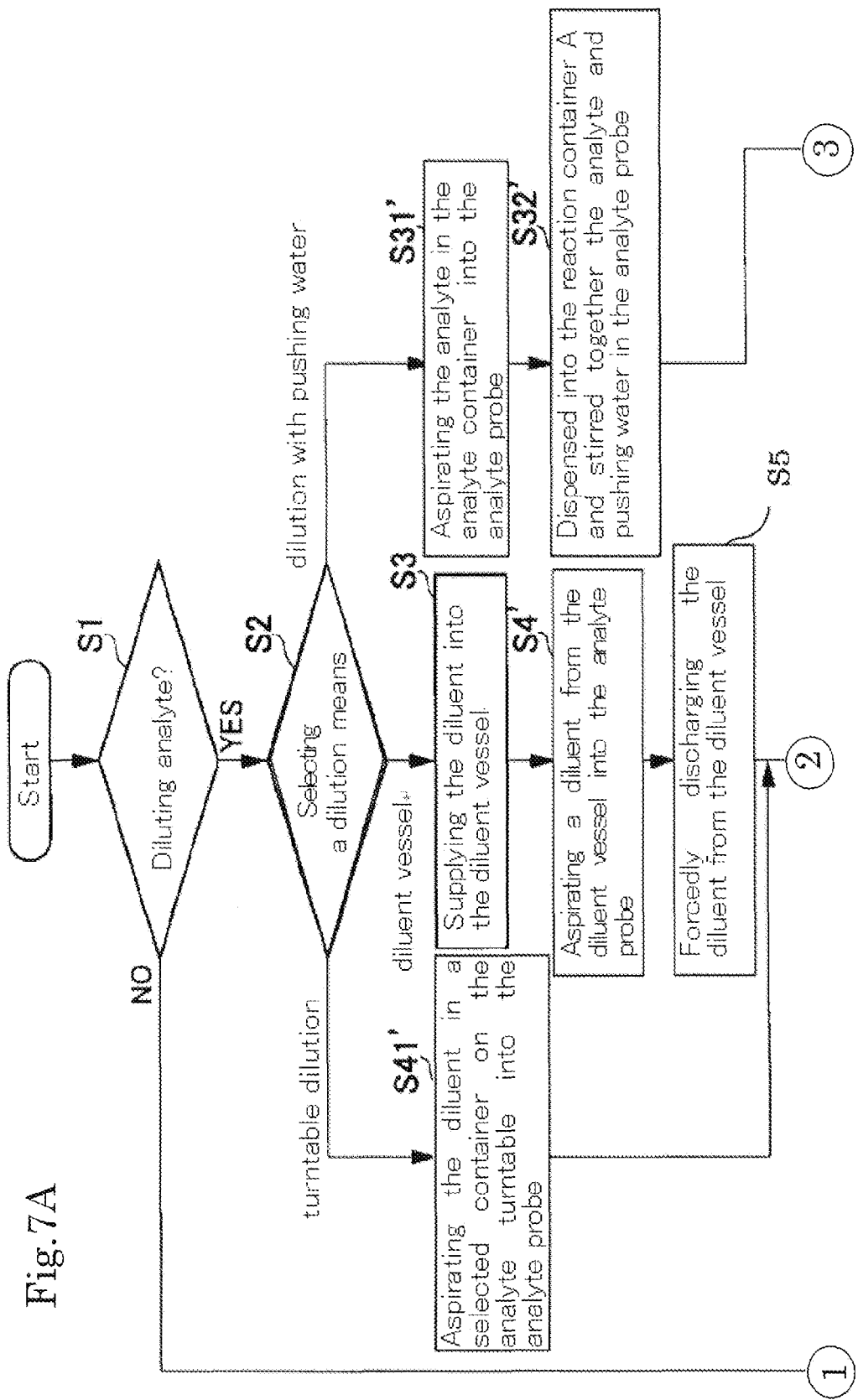
FIGS. 7A and 7B are flowcharts illustrating a method of automated analysis using the automated analyzer shown in FIG. 6.
Figure 7B:
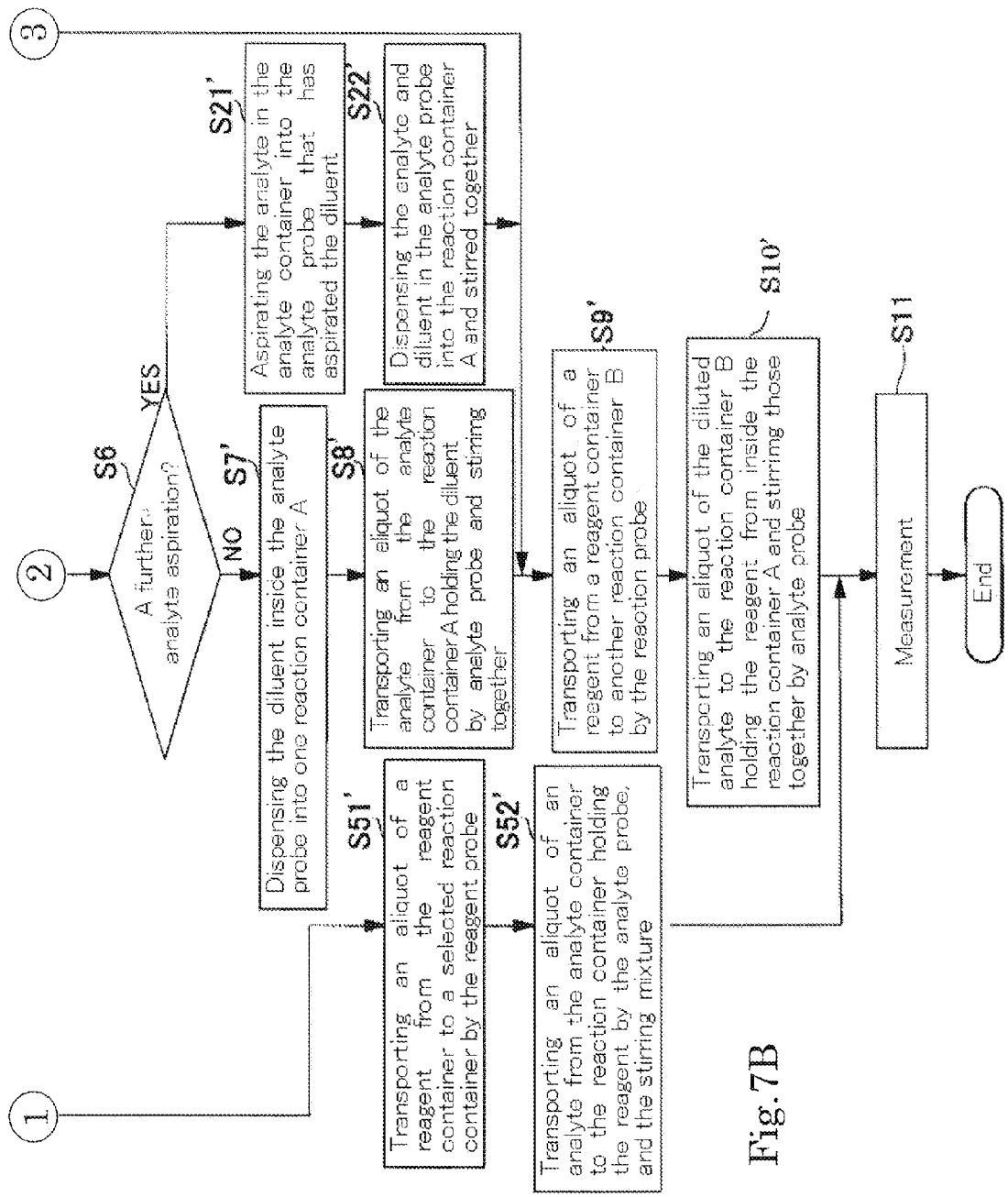

FIGS. 7A and 7B are flowcharts illustrating a method of automated analysis using the automated analyzer 2 according to the second embodiment. A procedure by which the method of automated analysis is implemented by the controller 41' of the automated analyzer 2 is described below by referring to the flowcharts of FIGS. 7A and 7B and to FIGS. 4 and 6. Note that a description of the operation for cleaning the probes is omitted but it is assumed that probes 31 and 37 are cleaned whenever an aliquotting operation ends.

Prior to the procedure of automated analysis illustrated in the flowcharts of FIGS. 7A and 7B, items of analysis and a control program to be run by the controller 41' are selected and set through the manual control portion 43 shown in FIG. 4. The analyte turntable 11 shown in FIG. 6 holds the plurality of analyte containers 11a storing analytes. The reaction containers 15a are held on the reaction turntable 15. Each reagent turntable 17 holds the reagent containers 17a storing reagents corresponding to the set items of analysis. The analysis is made to progress as follows.

Steps S1-S3 are performed in the same way as in the first embodiment.

Control goes from step S3 to step S4', where a diluent is aspirated from the diluent vessel into the analyte probe. In this step, the analyte probe 31 shown in FIG. 6 is inserted into the diluent vessel 21, and the diluent inside the diluent vessel 21 is aspirated.

Steps S5 to S6 are performed in the same way as in the first embodiment. In step S5, the diluent is forced out of the diluent vessel. In step S6, a decision is made as to whether or not an aspiration of the diluent is subsequently performed. The decision is NO indicating that no subsequent aspiration is performed, and control goes to the next step S7'.

In step S7', the diluent inside the analyte probe is dispensed into one reaction container A. In this step, the analyte probe 31 shown in FIG. 6 is moved into a position above the reaction container A of the reaction containers 15a held on the reaction turntable 15. The diluent is dispensed into this reaction container A.

In step S8', the analyte probe transports an aliquot of the analyte from the analyte container to the reaction container A holding the diluent, and the analyte and the diluent are stirred together. In this step, the analyte probe 31 shown in FIG. 6 aspirates the analyte from inside the given analyte container 11a held on the analyte turntable 11 and dispenses the aspirated analyte into the reaction container A storing the diluent on the reaction turntable 15. Then, the diluent and analyte stored in this reaction container A are stirred together by the stirrer (not shown) to prepare a diluted analyte.

In step S9', the reaction probe transports an aliquot of a reagent from a reagent container to another reaction container B. In this step, the reagent probe 37 shown in FIG. 6 aspirates the reagent from inside the reagent container 17a and dispenses the aspirated reagent into the reaction container B different from the reaction container A out of the reaction containers 15a held on the reaction turntable 15.

In step S10', the analyte probe transports an aliquot of the diluted analyte to the reaction container B holding the reagent from inside the reaction container A. In this step, the diluted analyte is first aspirated by the analyte probe 31 shown in FIG. 6 from inside the reaction container A storing the diluted analyte on the reaction turntable 15, and the aspirated diluted analyte is dispensed into the reaction container B storing the reagent on the reaction turntable 15. Then, the diluted analyte and the reagent stored in the reaction container B are stirred together by the stirrer (not shown).

In step S11, a measurement is performed. In this step, the reaction container B in which the diluted analyte and the reagent are stored in step S10' is moved into a position opposite to the measurement section 40 shown in FIG. 6. A measurement is carried out in the same way as in the first embodiment, and the present processing subroutine is ended.

If the decision at step S6 is YES indicating that a subsequent aspiration is performed, and if the "subsequent aspiration" of analyte is selected through the consecutive aspiration setting portion 43e of the manual control portion 43 already shown in FIG. 4, control goes to step S21'.

In this step S21', the analyte in the analyte container is aspirated into the analyte probe that has aspirated the diluent. That is, the diluent is aspirated into the analyte probe in step S4'. This is immediately followed by an aspiration of an analyte into the analyte probe that has aspirated the diluent. In this step, the diluent inside the diluent vessel 21 is aspirated by the analyte probe 31 shown in FIG. 6. This is immediately followed by an aspiration of the analyte from the given analyte container 11a held on the analyte turntable 11.

In step S22', the analyte and diluent in the analyte probe are dispensed into the reaction container A and stirred together. In this step, the analyte and diluent in the analyte probe 31 shown in FIG. 6 are dispensed into the reaction container A out of the reaction containers 15a on the reaction turntable 15 and stirred together by the stirrer (not shown). Thus, a diluted analyte is prepared. Subsequently, steps S9'-S11 are performed, and the measurement for the set items of analysis is ended.

In the above-described step S2, if "dilution with pushing water" is selected, control goes from step S2 to step S31', where the analyte in the analyte container is aspirated into the analyte probe. In this example, the analyte probe 31 shown in FIG. 6 is inserted into one analyte container 11a held on the analyte turntable 11 and the analyte in this analyte container 11a is aspirated.

In step S32', the analyte and pushing water in the analyte probe are dispensed into the reaction container A and stirred together. In this example, the pushing water in the analyte probe 31 shown in FIG. 6 is used as a diluent and dispensed into the reaction container A of the reaction containers 15a held on the reaction turntable 15 together with the analyte aspirated in the analyte probe 31. The water and the analyte are stirred together by the stirrer (not shown), thus preparing a diluted analyte. Then, steps S9'-S11 are performed. The measurement regarding the set items of analysis is ended.

If the decision at the step S2 is that "turntable dilution" is selected, control goes from step S2 to step S41', where the diluent in a selected container on the analyte turntable is aspirated into the analyte probe. In this example, the analyte probe 31 shown in FIG. 6 is inserted into the given analyte container 11a held on the analyte turntable 11, and the diluent in the analyte container 11a is aspirated. Then, steps S6-S11 are performed. The measurement for the set items of analysis is ended.

If the decision at the above-described step S1 is NO indicating that there is no analyte dilution, i.e., if "non-dilution" of analyte is selected through the dilution setting portion 43b of the manual control portion 43 already shown in FIG. 4, then it is determined that there is no analyte dilution (NO). Control goes to the next step S51'.

In this step S51', an aliquot of a reagent is transported from the reagent container to a selected reaction container by the reagent probe. In this example, the reagent in the reagent container 17a is aspirated by the reagent probe 37 shown in FIG. 6, and the aspirated reagent is dispensed into the reaction container 15a held on the reaction turntable 15.

In step S52', an aliquot of an analyte is transported from the analyte container to the reaction container holding the reagent by the analyte probe, and the mixture is stirred. In this example, an analyte is aspirated from the given analyte container 11a held on the analyte turntable 11 by the analyte probe 31 shown in FIG. 6 and dispensed into the reaction container 15a which holds the reagent and which is held on the reaction turntable 15. Then, the analyte and reagent stored in the reaction container 15a are stirred together by the stirrer (not shown). Then, step S11 is performed, and the measurement for the set items of analysis is ended.

This series of steps S1-S52' is performed repeatedly and successively for a plurality of analytes. Therefore, a decision step (not shown) may be provided after the step S11 to make a decision as to whether a measurement for a set number (n) of analytes is ended, and the steps S1-S52' may be repeated until it is determined that the number n is reached.

Advantageous Effects of Second Embodiment

The automated analyzer 2 according to the second embodiment described so far is so configured that a diluent is aliquotted from the diluent vessel 21 into the reaction containers 15a by the analyte probe 31 used to aliquot an analyte from the analyte container 11a into the reaction containers 15a. Especially, the diluent vessel 21 has the diluent discharging mechanism 25. Therefore, even if a slight amount of analyte is carried into the diluent vessel 21 by the analyte probe 31, carry-over of analyte in the diluent vessel 21 can be prevented by discharging the diluent in the diluent vessel 21 from the diluent discharging mechanism 25 and supplying new diluent into the diluent vessel 21 from the diluent supply mechanism 23 in the same way as in the first embodiment.

Furthermore, the automated analyzer 2 and method of automated analysis according to the second embodiment are so configured that diluent is supplied into the diluent vessel 21 from the diluent supply mechanism 23. Especially, the diluent vessel 21 storing only diluent is provided. Consequently, these analyzer and method according to the second embodiment can produce the same advantageous effects as the automated analyzer and method of automated analysis according to the first embodiment.

In the second embodiment described so far, in step S4', the diluent is aspirated into the analyte probe from the diluent vessel as shown in FIGS. 7A and 7B. Whenever this step ends, the diluent is forced out of the diluent vessel in step S5. Note that the manner in which the diluent is discharged from inside the diluent vessel is not restricted to this method. For example, where plural diluted analytes are created from the same analyte and analyzed successively, a decision step may be added to make a decision as to whether this series of analyses is complete. Whenever an operation for creating plural diluted analytes from one analyte ends, the diluent may be forced out of the diluent vessel.

Third Embodiment

Configuration of Automated Analyzer; Example of Aliquotting Diluent by Reagent Probe FIG. 8 schematically shows the configuration of an automated analyzer according to a third embodiment. This automated analyzer, 3, is similar to the automated analyzer according to the second embodiment except that a controller 41" aliquots a diluent by operation of any reagent probe 37 and that the diluent vessel 21 in the diluent supply portion 20 is disposed close to at least one of the reaction turntable 15 and reagent turntables 17. One of the reagent probes 37 is mounted in a position where it can be moved by its arm. It is assumed that the capacity of the diluent vessel 21 is approximately equal to or more than that of each reaction container 15a held on the reaction turntable 15.

Figure 9:
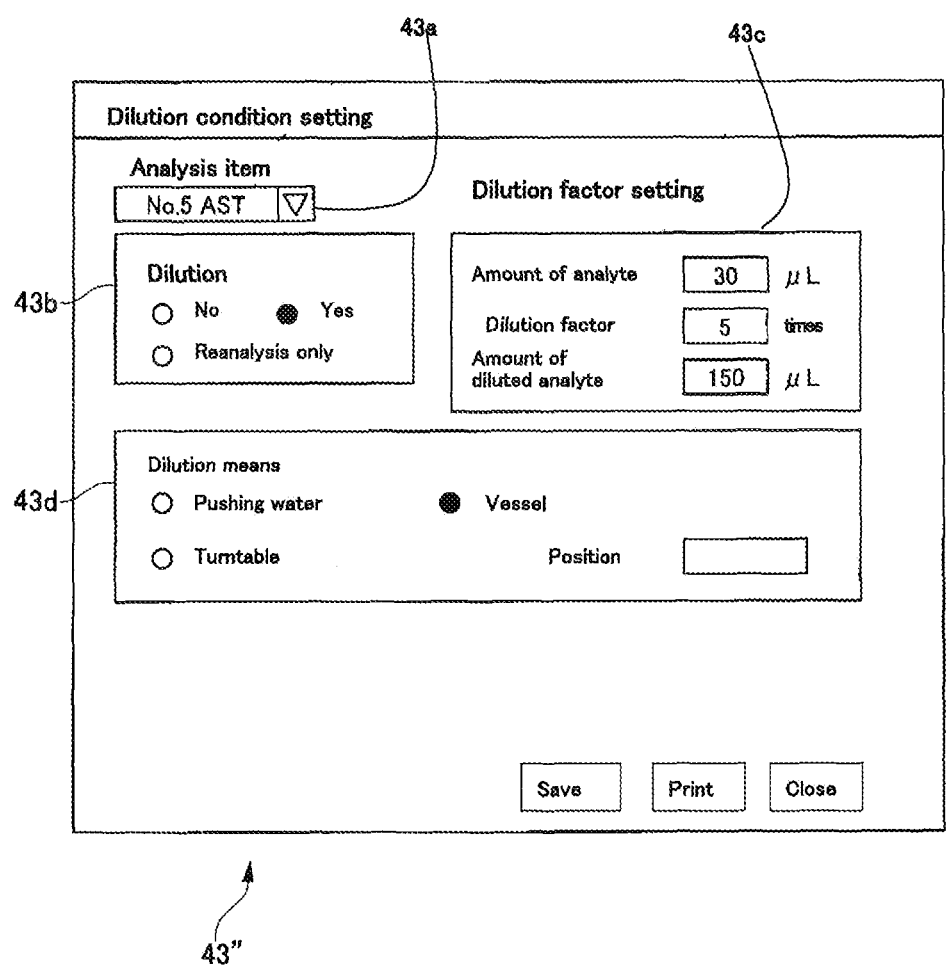
FIG. 9 is a schematic representation of a manual control portion of the automated analyzer shown in FIG. 8.

FIG. 9 schematically shows the configuration of a manual control portion 43" mounted in the automated analyzer 3. The illustrated manual control portion 43" is similar to the manual control portions of the analyzers according to the first and second embodiments except that the consecutive aspiration setting portion 43e (FIG. 4) is omitted.

Method of Automated Analysis

Figure 10A:
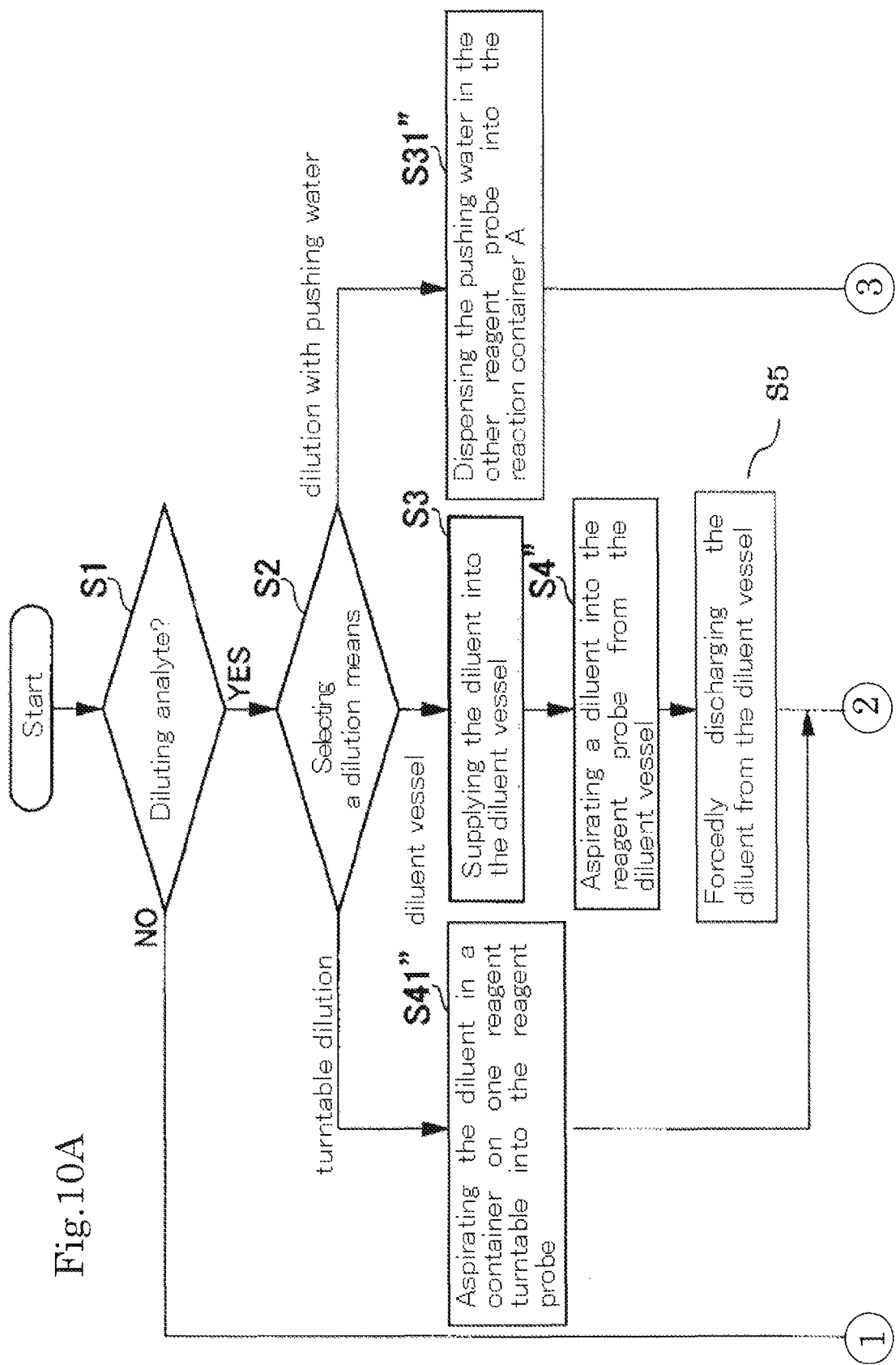
FIGS. 10A and 10B are flowcharts illustrating a method of automated analysis using the automated analyzer shown in FIG. 8.
Figure 10B:
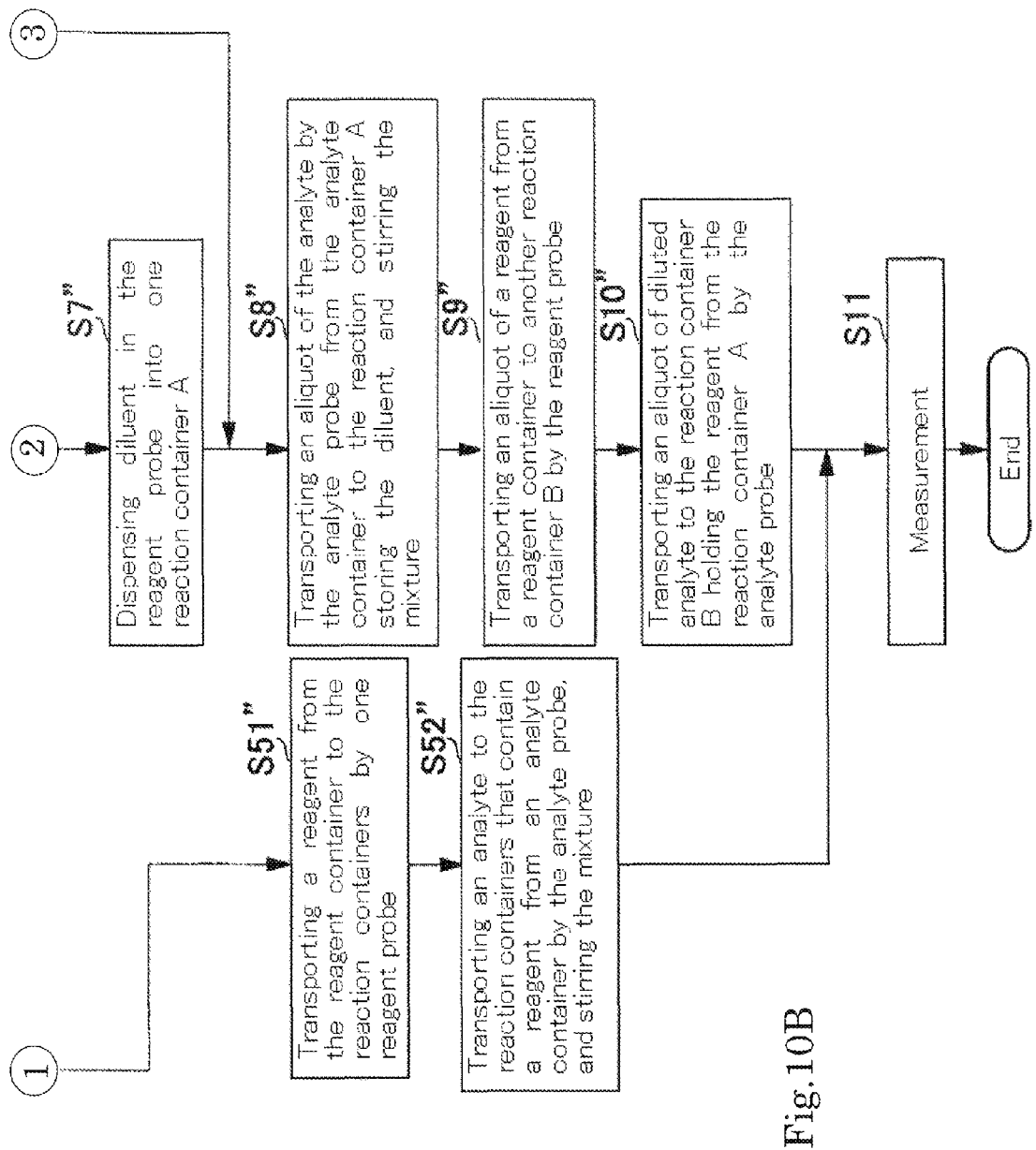

FIGS. 10A and 10B are flowcharts illustrating a method of automated analysis using the automated analyzer 3 according to the third embodiment. The procedure of the method of automated analysis executed by the controller 41" of the automated analyzer 3 is described below by referring to the flowcharts of FIGS. 10A and 10B and to FIGS. 8 and 9. A description of the operation of cleaning probes is omitted. It is assumed that the probes 31 and 37 are cleaned whenever an aliquotting operation ends.

Prior to the procedure of automated analysis illustrated in the flowcharts of FIGS. 10A and 10B, items of analysis and a control program to be run by the controller 41" are selected and set through the manual control portion 43" shown in FIG. 9. The analyte turntable 11 shown in FIG. 8 holds the plurality of analyte containers 11a storing analytes. The reaction containers 15a are held on the reaction turntable 15. Each reagent turntable 17 holds the reagent containers 17a storing reagents corresponding to the set items of analysis. Then, the analysis is made to progress as follows.

Steps S1-S3 are performed in the same way as in the first embodiment.

Control goes from step S3 to step S4", where a diluent is aspirated into the reagent probe from the diluent vessel. In this example, one reagent probe 37 shown in FIG. 8 is inserted into the diluent vessel 21 and the diluent inside the diluent vessel 21 is aspirated.

Step S5 is similar to step S5 of the first embodiment. In this step S5, the diluent is forced out of the diluent vessel.

In step S7", the diluent in the reagent probe is dispensed into one reaction container A. In this example, the reagent probe 37 shown in FIG. 8 is moved into a position lying above one reaction container A of the reaction containers 15a held on the reaction turntable 15, and the diluent is dispensed into this reaction container A.

In step S8", an aliquot of the analyte is transported by the analyte probe from the analyte container to the reaction container A storing the diluent, and the mixture is stirred. In this step, the analyte is aspirated from inside the given analyte container 11a held on the analyte turntable 11 by the analyte probe 31 shown in FIG. 8, and the aspirated analyte is dispensed into the reaction container A storing the diluent on the reaction turntable A. Then, the diluent and analyte stored in the reaction container A are stirred together by the stirrer (not shown), thus creating a diluted analyte.

In step S9", an aliquot of a reagent is transported from a reagent container to another reaction container B by the reagent probe. In this step, the reagent in a selected one of the reagent containers 17a is aspirated by the other reagent probe 37 shown in FIG. 8, and the aspirated reagent is dispensed into the reaction container B of the reaction containers 15a held on the reaction turntable 15, the container B being different from the aforementioned reaction container A.

In step S10", an aliquot of diluted analyte is transported to the reaction container B holding the reagent from the reaction container A by the analyte probe. In this step, the analyte probe 31 shown in FIG. 8 aspirates the diluted analyte from inside the reaction container A storing the analyte diluted with the diluent on the reaction turntable 15 and dispenses the aspirated analyte into the reaction container B storing the reagent on the reaction turntable 15. Then, the diluted analyte and the reagent stored in the reaction container B are stirred together by the stirrer (not shown).

In step S11, a measurement is performed. In this step, the reaction container B in which the diluted analyte and the reagent are stored in step 10" is moved into a position located opposite to the measurement section 40 shown in FIG. 8, a measurement is carried out in the same way as in the first embodiment, and the present subroutine is ended.

If the decision at the above-described step S2 is that "dilution with pushing water" is selected, control goes from step S2 to step S31", where the pushing water in the other reagent probe 37 is dispensed into the reaction container A. In this step, the pushing water in the other reagent probe 37 shown in FIG. 8 is dispensed into the reaction container A of the reaction containers 15a held on the reaction turntable 15. Then, steps S8"-S11 are performed. The measurement for the set items of analysis is ended.

If the decision at step S2 is that "turntable dilution" is selected, control goes from step S2 to step S41", where the diluent in a container on one reagent turntable is aspirated into the reagent probe. In this step, the other reagent probe 37 shown in FIG. 8 is inserted into the given reagent container 17a held on the reagent turntable 17 and the diluent is aspirated from inside the reagent container 17a. Then, steps S7"-S11 are performed. The measurement for the set items of analysis is ended.

If the decision at the step S1 is NO indicating that the analyte is not diluted, i.e., "non-dilution" of analyte is selected through the dilution setting portion 43b of the manual control portion 43" already shown in FIG. 9, it is determined that there is no dilution (NO). The control goes to the next step S51".

In this step S51", a reagent is transported from the reagent container to the reaction containers by one reagent probe. Specifically, the other reagent probe 37 shown in FIG. 8 aspirates the reagent in the reagent container 17a and dispenses the aspirated reagent into the reaction containers 15a held on the reaction turntable 15.

In step S52", an analyte is transported to the reaction containers that contain a reagent from an analyte container by the analyte probe, and the mixture is stirred. In particular, the analyte probe 31 shown in FIG. 8 aspirates the analyte from inside the given analyte container 11a held on the analyte turntable 11 and dispenses the aspirated analyte into the reaction containers 15a holding the reagent and held on the reaction turntable 15. Then, the analyte and reagent stored in the reaction containers 15a are stirred together by the stirrers (not shown). Then, step S11 is performed, and the measurement for the set items of analysis is ended.

The series of steps S1-S52" described so far is performed repeatedly and successively for a plurality of analytes. Therefore, a decision step (not shown) may be provided after the step S11 to make a decision as to whether measurements for a set number (n) of analytes are ended, and the steps S1-S52" may be repeated until it is determined that the number n is reached.

Advantageous Effects of Third Embodiment

The automated analyzer 3 according to the third embodiment as described so far is so configured that a diluent is aliquotted from the diluent vessel 21 into the reaction containers 15a by one reagent probe 37 for injecting aliquots of an analyte from the reagent container 17a into the reaction containers 15a. Especially, the diluent vessel 21 has the diluent discharging mechanism 25. Therefore, if a slight amount of reagent is carried into the diluent vessel 21 by the reagent probe 37, contamination of the diluted analyte due to carry-over of reagent in the diluent vessel 21 can be prevented by discharging the diluent in the diluent vessel 21 from the diluent discharging mechanism 25 and resupplying diluent into the diluent vessel 21 from the diluent supply mechanism 23 in the same way as in the first embodiment.

In the automated analyzer 3 and method of automated analysis according to the third embodiment, diluent is supplied into the diluent vessel 21 from the diluent supply mechanism 23. Especially, the diluent vessel 21 storing only diluent is provided. Consequently, the same advantageous effects as the automated analyzer and method of automated analysis according to the first embodiment can be obtained.

Having thus described our invention with the detail and particularity required by the Patent Laws, what is desired protected by Letters Patent is set forth in the following claims.

The invention claimed is:

1. An automated analyzer comprising:
container holders for holding containers in which a liquid is stored;
a probe for aspirating and dispensing the liquid between two of the containers held by the container holders;
a diluent vessel having a top opening for storing a diluent, said vessel positioned within range of the probe such that the probe can be inserted into the top opening to aspirate a portion of the diluent and thereafter be removed; and
a diluent supply mechanism for supplying the diluent into the diluent vessel via a first conduit,
wherein said probe has a function of aliquoting a portion of the diluent stored in the diluent vessel into any one of the containers held by the container holders, and
wherein said diluent vessel has a diluent discharging mechanism for discharging the diluent remaining in the diluent vessel from inside the diluent vessel via a second conduit having a valve therein after the probe is removed.

2. The automated analyzer as set forth in claim 1, further comprising a controller for controlling said diluent discharging mechanism including the valve in the second conduit when said portion of the diluent is aspirated by said probe such that the diluent remaining in the diluent vessel is discharged after the end of the aspiration of the portion of the diluent from inside the diluent vessel by the probe.

3. The automated analyzer as set forth in claim 2, wherein said controller controls said diluent discharging mechanism such that the diluent remaining in said diluent vessel is discharged whenever the aspiration of the diluent by said probe from inside the diluent vessel ends.

4. The automated analyzer as set forth in claim 1, wherein said container holders have a function of transporting the held containers, and wherein said diluent vessel is disposed close to at least one of said container holders.

5. The automated analyzer as set forth in claim 1, wherein said probe dispenses aliquots of a liquid between said containers held on two different ones of said container holders.

6. The automated analyzer as set forth in claim 1, further comprising an arm that causes said probe to be freely moved in orbits that pass over the containers held by said container holders and in orbits that pass over said diluent vessel and causes the probe to be moved up and down freely.

7. A method of automated analysis comprising the steps of:
aspirating a liquid from a first container by a probe for aspirating and dispensing liquid;
dispensing the aspirated liquid in the probe into a second container;
supplying via a first conduit a diluent into a diluent vessel having a top opening arranged in a position where the probe can be inserted to aspirate diluent through the top opening;
inserting the probe into the diluent vessel and aspirating a portion of the diluent in the diluent vessel by the probe and withdrawing the probe from the diluent vessel;
dispensing the aspirated diluent in the probe into the second container;
repeating these steps in a given procedure for a plurality of analytes; and
discharging the diluent remaining in the diluent vessel via a second conduit after every time the probe is inserted in the diluent vessel, the diluent is aspirated by the probe and the probe is removed from the diluent vessel.

8. The method of automated analysis as set forth in claim 7, wherein the step of aspirating the liquid from said first container by said probe and the step of aspirating the diluent in said diluent vessel by the probe are performed consecutively, and wherein the step of dispensing the aspirated liquid in the probe into said second container and the step of dispensing the aspirated diluent in the probe into the second container are performed at the same time.

9. An automated analyzer comprising:
an analyte turntable for holding a plurality of analyte containers in which an analyte is stored;
a dilution turntable for holding a plurality of diluent containers for storing the analyte diluted with a first diluent;
a reaction turntable for holding a plurality of reaction containers for reacting the analyte with a reagent;
a diluent probe for aspirating the analyte from a selected one of the analyte containers held on the analyte turntable and injecting an aliquot portion of the aspirated analyte into the diluent containers on the dilution turntable together with the first diluent;
a sample probe for aspirating the diluted analyte from a selected one of the dilution containers held on the dilution turntable and dispensing an aliquot of the aspirated diluted analyte into the reaction containers on the reaction turntable;
a diluent vessel operative to store a second diluent and having a top opening and located within a range of the diluent probe such that the probe can be inserted via the opening to aspirate a portion of the second diluent and thereafter is removed;
a diluent supply mechanism for supplying the second diluent into the diluent vessel via a first conduit;
a diluent discharging mechanism for discharging the second diluent remaining in the diluent vessel via a second conduit; and
a controller programmed to control the diluent probe, the diluent supply mechanism, and the diluent discharging mechanism, the controller controlling (1) the diluent probe such that a portion of the second diluent is aspirated from the diluent vessel and an aliquot portion is dispensed into the dilution containers and (2) the diluent discharging mechanism such that a portion of the second diluent remaining in the diluent vessel is discharged from the diluent vessel by the diluent discharging mechanism during a period beginning with an end of the aspiration of a portion of the second diluent from the diluent vessel by the diluent probe and ending with a start of a next aspiration and then (3) the diluent supply mechanism such that the diluent vessel is filled with the second diluent by the diluent supply mechanism.

10. An automated analyzer comprising:
an analyte turntable for holding a plurality of analyte containers in which an analyte is stored;
a reagent turntable for holding reagent containers holding reagents therein;
a reaction turntable for holding a plurality of reaction containers each for reacting an analyte with a reagent;

a sample probe for aspirating the analyte from a selected one of the analyte containers held on the analyte turntable and aliquoting the aspirated analyte into the reaction containers on the reaction turntable;

a reagent probe for aspirating a reagent from a selected one of the reagent containers held on the reagent turntable and dispensing the aspirated reagent into the reaction containers on the reaction turntable;

a diluent vessel operative to store a diluent, said diluent vessel having a top opening and located within a range of the sample probe or the reagent probe such that the sample probe or the reagent probe can be inserted via the opening to aspirate a portion of the diluent and is removed;

a diluent supply mechanism for supplying the diluent into the diluent vessel via a first conduit;

a diluent discharging mechanism for discharging the remaining diluent in the diluent vessel via a second conduit; and a controller programmed to control the sample probe or the reagent probe, the diluent supply mechanism, and the diluent discharging mechanism, the controller being programmed to control (1) the sample probe or the reagent probe such that a portion of the diluent is aspirated from the diluent vessel and the aspirated diluent is dispensed into the reaction containers and (2) the diluent discharging mechanism such that the diluent remaining in the diluent vessel is discharged from the diluent vessel by the diluent discharging mechanism during a period beginning with an end of the aspiration of a portion of the diluent from the diluent vessel by the sample probe or the reagent probe and ending with a start of a next aspiration and then (3) the diluent supply mechanism such that the diluent vessel is filled with the diluent by the diluent supply mechanism.

\* \* \* \* \*